(12) United States Patent
Da Silva et al.

(10) Patent No.: US 8,835,489 B2
(45) Date of Patent: Sep. 16, 2014

(54) COMPOUNDS OF THE PTEROCARPANQUINONE FAMILY, METHOD FOR PREPARING THE SAME, PHARMACEUTICAL COMPOSITION CONTAINING THE NEW COMPOUNDS OF THE PTEROCARPANQUINONE FAMILY, USES AND THERAPEUTIC METHOD

(75) Inventors: Alcides Jose Monteiro Da Silva, Duque de Caxias (BR); Vivian Mary Barral Dold Rumjanek, Rio de Janeiro (BR); Bartira Rossi Bergmann, Rio de Janeiro (BR); Eduardo Salustiano Jesus Dos Santos, Rio de Janeiro (BR); Paulo Roberto Ribeiro Costa, Rio de Janeiro (BR); Chaquip Daher Netto, Rio de Janeiro (BR); Wallace Pacienza Lima, Rio de Janeiro (BR); Eduardo Caio Torres Dos Santos, Rio de Janeiro (BR); Moises Clemente Marinho Cavalcante, Rio de Janeiro (BR); Sergio Henrique Seabra, Rio de Janeiro (BR); Ingred Goretti Rica, Rio de Janeiro (BR)

(73) Assignee: Universidade Federal Do Rio de Janeiro, Rio de Janeiro (BR)

( * ) Notice: Subject to any disclaimer, the term of this patent is extended or adjusted under 35 U.S.C. 154(b) by 402 days.

(21) Appl. No.: 13/127,797

(22) PCT Filed: Nov. 5, 2009

(86) PCT No.: PCT/BR2009/000364
§ 371 (c)(1),
(2), (4) Date: May 5, 2011

(87) PCT Pub. No.: WO2010/054452
PCT Pub. Date: May 20, 2010

(65) Prior Publication Data
US 2011/0224289 A1    Sep. 15, 2011

(30) Foreign Application Priority Data
Nov. 6, 2008    (BR) .............................. PI 0806047-9

(51) Int. Cl.
*A61K 31/35*    (2006.01)
*C07D 311/94*    (2006.01)
*C07D 493/04*    (2006.01)

(52) U.S. Cl.
CPC ........... *C07D 493/04* (2013.01); *C07B 2200/07* (2013.01)
USPC ........................................... 514/453; 549/382

(58) Field of Classification Search
CPC ..... A61K 31/35; A61K 31/352; C07D 493/04
USPC .......................................... 549/382; 514/453
See application file for complete search history.

(56) References Cited

U.S. PATENT DOCUMENTS 5,721,371 A    2/1998   Larock

FOREIGN PATENT DOCUMENTS

EP    0089229    9/1983
JP    6-312983   11/1994

OTHER PUBLICATIONS

A.J.M. da Silva et al., Synthesis and Preliminary Pharmacological Evaluation of New (±) 1,4-Naphtho-quinones Structurally Related to Lapachol. Bioorganic & Medicinal Chemistry, 10, 2002, 2731-2738.
A.J.M da Silva et al., The First Synthesis of (±)-3,4-Dihydroxy-8,9-methylenedioxypterocarpan, an Antitu-moral Agent and its Coumestan Derivative, Journal of the Brazilian Chemical Society, 15(6), 2004, 979-981.
E.S.C. Pôças et al., Structure-activity relationship of wedelolactone analogues: Structural Requirements for inhibition of $Na^{30}$, $K^{+}$-ATPase and binding to the central benzodiazepine receptor. Bioorganic & Medicinal Chemistry, 14, 2006, 7962-7966.
P. Muriel et al., Insights into the Mechanism of Erythrocyte $Na^{+}/K^{+}$-ATPase Inhibition by Nitric Oxide and Peroxynitrite Anion, Journal of Applied Toxicology, 23, 2003, 275-278.

*Primary Examiner* — Andrew D Kosar
*Assistant Examiner* — Raymond Covington
(74) *Attorney, Agent, or Firm* — Fildes & Outland, P.C.

(57) ABSTRACT

This invention belongs to the chemical-pharmaceutical field. New compounds of pterocarpanquinone family presented in formula (I) according to this invention are capable to be activated by reduction generating alkylating species intracellularly. It presents selective cytotoxic effects particularly on mammalian human and nonhuman cells that divide constantly and are useful in treating diseases and dysfunctions related to the phenomenon of undesired cell proliferation. Such compounds are also effective for the treatment of diseases or dysfunctions related to high levels of TNF-α in human and nonhuman mammals.

29 Claims, 2 Drawing Sheets

Figure 1:
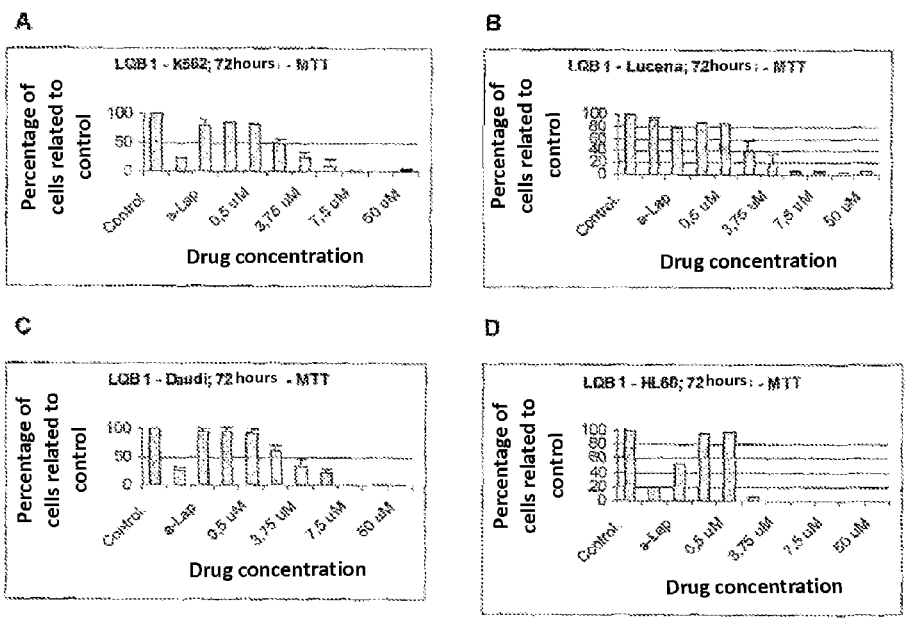

COMPOUNDS OF THE PTEROCARPANQUINONE FAMILY, METHOD FOR PREPARING THE SAME, PHARMACEUTICAL COMPOSITION CONTAINING THE NEW COMPOUNDS OF THE PTEROCARPANQUINONE FAMILY, USES AND THERAPEUTIC METHOD

TECHNICAL FIELD

This invention belongs to the chemical-pharmaceutical field. New compounds of pterocarpanquinone family presented in this invention are capable to be activated by reduction generating alkylating species intracellularly. It presents selective cytotoxic effects particularly on mammalian human and nonhuman cells that divide constantly and are useful in treating diseases and dysfunctions related to the phenomenon of undesired cell proliferation. Such compounds are also effective for the treatment of diseases or dysfunctions related to high levels of TNF-α in human and nonhuman mammals.

This invention also refers to an economical and ecologically viable production process for new compounds of pterocarpanquinone family.

The use of these new compounds and pharmaceutical composition containing these compounds are also scope of this invention.

PREVIOUS TECHNIQUES

Cancer is a major public health problem worldwide, indiscriminately affecting all strata of society. It occurs in around seven million people per year and the second leading cause of death disease in the U.S.; according to the National Cancer Institute (INCA), among 11.4% to 13.7% of total deaths in Brazil is directly related to neoplasms, being the third largest risk factor for mortality in the country.

Due to the large investment in pharmaceutical laboratories development of new therapeutic agents for cancer treatment, a variety of drugs are available for clinical use. However, the high toxicity generally associated with these substances and the development of cell lines with the phenotype of multidrug resistance (MDR) requires a continuous effort aimed at development of new therapeutic agents.

In contrast, therapeutic advances have been much more modest when it comes to fighting the parasite. This reflects the lack of interest and private sector investments, since parasites such as malaria, leishmaniasis and Chagas disease, for example, affect mainly low-income populations in Africa, Asia and South America.

Neglected by the private sector, control leishmaniasis depends almost exclusively on government initiatives (universities, research institutes and laboratories officers) and there is a great need for alternatives to chemotherapy. The therapeutic approach for these parasites is complicated by the emergence of resistance, as we mentioned to the anticancer agents, and there are such cases the need for a continuing effort aimed at developing new drugs.

Some molecular targets are common to anticancer agents and pesticides, such as DNA and enzymes of DNA biosynthesis machinery. However, these enzymes have small structural differences (isoforms) depending on the species, which makes possible the discovery of bioselective inhibitors.

In the case of parasitic diseases, bioselective can also be achieved by the choice of biological targets that are not present in human cells, exploiting the differences in the physiology of these organisms in relation to human cells.

Substances developed for cancer treatment may find a therapeutic application as antiparasitic agents. Like miltefosine, a "alkylfhosfholipid" developed and licensed by the Indian government in March 2002 for the treatment of visceral leishmaniasis orally, which is currently in phase IV clinical trial involving 1,200 patients (Sindermann, 2006). Another example is paromomycin, an aminoglycoside antibiotic, a drug that is being tested in formulations for the topical treatment of cutaneous leishmaniasis in the New World. Its use has proved more efficient than the parenteral antimony composites. The case of artemisinin is also noteworthy. The potent antimalarial action and the new mechanism of action of this terpenoid led to the development of a large number of derivatives, which were also evaluated as anticancer agents. The clinical application of these derivatives is recommended both for the treatment of malaria and certain types of cancer (Vennerstom, 2005; Posner, 2002, 2003, 2004, 2004; Chen, 1996). Finally, atavaquona, a naphthoquinone originally investigated for its anticancer properties, has been used in therapy as antiprotozoal. It is effective in the treatment of *Pneumocystis carinii* pneumonia and, in combination with proguanil, is used to treat and prevent malaria. In combination with azithromycin, is used to treat babeslosis. Its use for the treatment of cutaneous leishmaniasis was recommended in a recent publication.

Methotrexate is an inhibitor of folic acid synthesis. As folic acid is essential to the synthesis of DNA chain, this substance has been used clinically as an anticancer drug. However, its derivative trimetrexate has antiparasitic action against *Pneumocystis carinii*.

"Topoisomerase" inhibitors are frequently used in the treatment of malignancies and in the treatment of parasitic infections, like pentavalentantimonials and 9—"anilinoacridine".

Glutathione (GSH) is an enzyme that protects the *Plasmodium falciparum* from oxidative stress reactive of oxygen species (ERQ) (particularly —OH). The maintenance of intracellular levels of GSH depends basically on the reduction of "thioperoxide" GS-SG to GSH, catalyzed by glutathione reductase (GR). This enzyme has been exploited in the design of substances with antimalarial action. It was shown that inhibition of glutathione S-transferases (GST) by agents of antimalarialsquinone nature can be used to inhibit resistance to antineoplastic agents.

In 1863, Virchow described the occurrence of leukocyte infiltration in tumor tissue and thereby launched the hypothesis that the origin of cancer was related to sites of chronic inflammation (BalkwiH and Mantovani, 2001). Since then, several studies have confirmed this relationship between cancer and inflammation. Approximately 25% of all cases of cancer have the contribution of chronic infection and inflammation (Hussain and Harris, 2007). Intestinal inflammation, for example, is associated with colon, prostate and pancreatic carcinomas are associated with inflammation in such organs. Smoking and exposure to silica are also associated with lung inflammation and cancer, many infectious agents cause both inflammation and cancer (Itzkowitz and Yio, 2004, Nelson et al, 2004; Whitcomb, 2004, Lin and Karin, 2007). In fact, inflammation may contribute to each stage of tumor development (Lin and Karin, 2007). Many agents such as viruses and chemicals that promote inflammation also induced somatic alterations. Reactive oxygen species and nitrogen-induced inflammation, which serve to fight infection, also cause DNA damage in host cells. These changes, known as initiation, can be kept on a normal tissue until the cells began to be stimulated to grow in a process called promotion. Inflammatory factors released in the middle can act as promoters, since these factors stimulate tissue regeneration, but also induce cell proliferation and resistance to apoptosis in tumor cells. Finally, these same factors facilitate the invasion and metastasis of tumor cells, culminating in the progression, the last stage of carcinogenesis (Coussens and Werb, 2002; Lin and Karin, 2007).

Among the factors that regulate inflammatory cancer, cytokines and chemokines are the major players involved in tumor development. These molecules can act as mediators of the relationship between tumor and host cells (Kundu and Surh 2008). Inflammatory mediators such as cytokines and chemokines, are responsible for the recruitment of leukocytes from the bloodstream to the inflammatory (Sacca et al. 1997, Yang et al., 1998). They promote the expression of adhesion molecules on endothelial cells, which allow the passage of leukocytes into the inflamed tissue (Slease et al, 1998).

On inflammatory process TNF-α is a proinflammatory cytokine important role in the innate response of vertebrates (Varfolomeev and Ashkenazi, 2004). Since two decades TNF-α is described as the chief mediator in the pathogenesis of septic shock (Beutler et al., 1985). This cytokine is one of the most abundant secreted by macrophages. Several other cells, such as neutrophils, natural killer cells (NK) and T cells, are capable of release it when stimulated with LPS (Goetz et al., 2004).

TNF-α is synthesized as a precursor which is anchored to the plasma membrane. To pass the active form, pro-TNF-α is hydrolyzed by converting enzyme TNF-u (TACE), a metalloproteinase, releasing the soluble form of 17 KDa (Barbara et al. 1996; Moss, 1997).

To exert their biological activities, TNF-α should bind to membrane receptors. Two distinct receptors that can bind to TNF-α with high affinity are known: TNF-R1 and TNF-R2. According to Barbara (1996) and Chen (2002), TNF-R1 was the most active and thus begins the most biological responses.

The binding of TNF-α to the extracellular domain of TNF-R1 results in its trimerization, releasing a protein, known as silencer of death domains (SOOO) of the intracellular domain (CCD) to TNF-R1. The free ICD is recognized by an adapter death domain protein associated to TNF receptor (TRADD). This binds to the receptor protein that attracts and interacts with receptor RIP (Ting et al., 1996), factor associated with the TNF receptor (TRAF2) and protein with death domain associated with Fas (FADO) (Chen and Goeddel, 2002).

Depending on the stimulus, TNF-R1 can activate three different pathways of intracellular signaling. One of them leads to apoptosis through the FADO, which recruits caspase-B complex to the TNF receptors, unlocking a sequence of reactions that culminates in cell death. A second signal is through the action of TRAF2 signaling for apoptosis inhibitors, such as cellular inhibitor of apoptosis protein 1 and 2 (cIAP-1 and cIAP-2). This pathway is also capable of activating the MAP kinase pathway and the NF-kB. The third way is linked to activation of the IKK enzyme complex responsible for activation of NF-kB (Chen and Goeddel, 2002).

The suppression of TNF-α is already a recognized tool, including in the clinic for the treatment of inflammatory diseases. Currently, new compounds have been synthesized as analogues of thalidomide, which has severe side effects such as potent inhibitors of TNF-α, to be used as anti-inflammatory drugs (Hutchison et al, 2008; Lima et al., 2002).

Although firstly discovered as a factor that induces tumor necrosis, hence its name, some years ago it was knew that this apparently antineoplastic effect only occurs when TNF-α is administered locally and at higher concentrations which leads to numerous side effects such as fever, anemia, weight loss and fatigue and was therefore discarded as anticancer therapy (Slosarek & Balkwill, 2003). Several studies have associated the endogenous TNF-α as an inducer of tumor growth and facilitates tumor invasion and metastasis in TNF-α is responsible for inducing tumors in the production of tumor survival factors, by increasing mobility, tumor invasion and increase endurance to cytotoxic drugs, among other effects that favor the establishment and tumor progression (Slosarek et al, 2006; Wu et al; 1999, Shin et al., 2000). For these reasons, therapies involving inhibition of TNF-α in the treatment of cancers are already being proposed. More recent studies indicates treatment with inhibitors of TNF-α an important tool in the reduction of tumors and inhibition of metastasis (Waterston et al., 2004, Stasi et al., 2005; Glasmacher et al., 2005).

In addition to neoplasms TNF-α is related to other diseases such as rheumatoid arthritis, spongilitesanquiloisante, Crohn's disease, psoriasis, viral infections like hepatitis and AIDS, and bacterial infections like leprosy, tuberculosis, brucellosis, and trypanosomiasis parasites as and leishmaniasis.

Drigo et al in 2006 demonstrated that the progression of cardiomyopathy associated with Chagas disease is directly related to serum levels of TNF-alpha in patients with this cardiomyopathy who had heart failure. The use of Etanercept, a TNF-alpha blocker, during the chronic stage of Chagas disease attenuated the development of cardiomyopathy associated with Chagas disease (Bilate et al, 2007).

Polymorphic variations in the promoter region of TNFA gene has been associated with severe forms of infections like malaria, meningitis, leprosy and human and bovine brucellosis (Caballero et al, 2000, McGuire et al, 1994; Cabrera et al, 1995; swam et al, 1996, Roy et al 1997).

Recently, Silva et al, have developed a new family of chemical compounds called first generation "pterocarpanquinone", which consist of a pentacyclic skeleton shown in FIG. 1, where A and B rings (naphthoquinone system) replaced an oxygenated aromatic ring present in the structure of pterocarpanes.

The cytotoxic action of these first generation naphthoquinonespentacyclic was assessed in cell lines of breast cancer (MCF-7) (da Silva, 2002), leukemia (K562, Jurkat, Daudi, Raji, HL-60), including on the line Lucena I (phenotype MOR) (Netto, 2008) and lung (A549 and H460, the MDR phenotype). The results obtained with cells in phenotype MOR, show that these substances are not substrates for efflux pumps in these cells (Litman, 2001; Juranka, 1989). First generation "pterocarpanquinone" were also evaluated in *Leishmania amazonensis* and *Plasmodium falciparum* (chloroquine resistant strain) in culture (Netto, 2008c), being very effective against these protozoa. On the other hand, had low toxicity (high bioselective) to PHA-activated lymphocytes and murine lymphocytes (da Silva, 2008).

Second generation "pterocarpanquinone" were also synthesized (da Silva, 2008), where the originally D ring of 5 members had been replaced by a ring of 6 members. These substances also had toxic effects in cell lines MCF-7 and *Leishmania amazonensis* and *Plasmodium falciparum* (chloroquine resistant strain) in culture (Netto, 2008c), being also very effective against these protozoa. Also second generation "pterocarpanquinone" had low toxicity (high bioselective) to PHA-activated lymphocytes and murine lymphocytes (da Silva, 2008).

It has been shown (Netto, 2007) that the first generation "pterocarpanquinone", like mitomycin and anthracycline analogues and kalfungina (a naphthoquinone), are activated by reduction, being able to react with tiafanai, used as model biological nucleophiles. Thus, in addition to cytotoxicity by all quinones, due to the redox mechanism that ultimately leads to oxidative stress, first generation "pterocarpanquinone" can act as precursors of reactive intermediates generated in situ. This possible mechanism of action is especially interesting in the case of tumors where the central region, poorly vascularized, receives small supply of oxygen and is not exposed to oxidative stress. This possible mechanism of action may be related to the activity of these molecules in cells resistant to oxidative stress.

The production process of these first and second generation pterocarpanquinone, however, is uneconomical because it requires key step in the synthetic procedure a reaction mediated by stoichiometric amounts of palladium. Another problem is the use of phenol containing mercury in their structures, a fact that makes this production process environmentally unsuitable and inappropriate for the production of pharmaceuticals.

SUMMARY OF THE INVENTION

New compounds of pterocarpanquinone family with general formula (I):

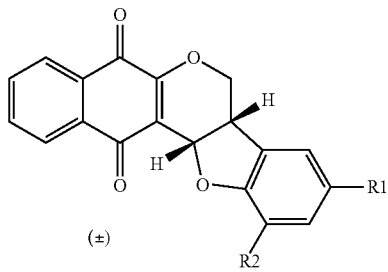

I (±)

its salts, solvates and racemates are an object of this invention. New compounds of pterocarpanquinone family has the ability to be activated by reduction, alkylating species generated intracellularly and is therefore useful in treating diseases and dysfunctions related to the phenomenon of undesired cellular proliferation and, in the treatment of diseases and/or dysfunctions related to high levels of TNF-α in a mammal human and/or nonhuman.

The second object of this invention is the production of new compounds of pterocarpanquinone family with general formula (I):

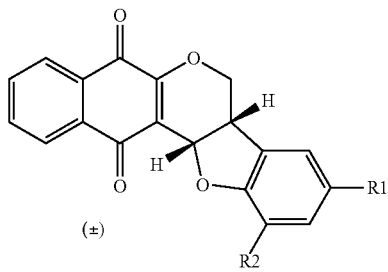

I (±)

theirs salts, solvates and racemates economically viable and ecologically compatible.

A third object of this invention is a pharmaceutical composition containing new compounds of pterocarpanquinone family with general formula (I):

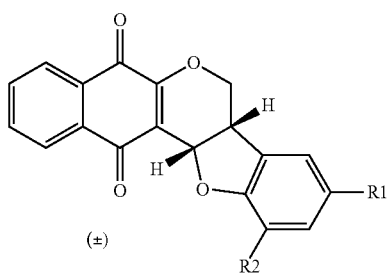

I (±)

and/or theirs salts, solvates and racemates to treat diseases or dysfunctions related to the phenomenon of undesired cellular proliferation in human or non-human mammals.

The fourth object of this invention relates to a pharmaceutical composition containing new compounds of pterocarpanquinone family with general formula (I):

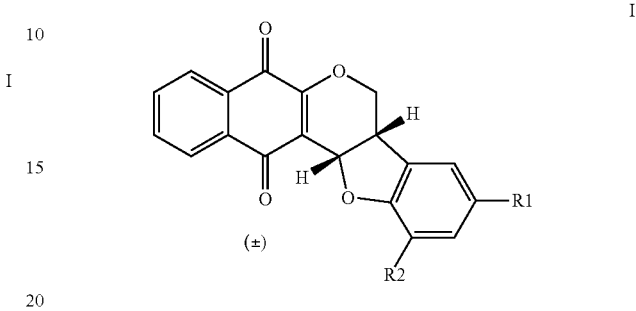

I (±)

and/or theirs salts, solvates and racemates to treat diseases or dysfunctions related to increased levels of TNF-α in human or non-human mammals.

The fifth object of this invention comes from the use of new compounds of formula (I):

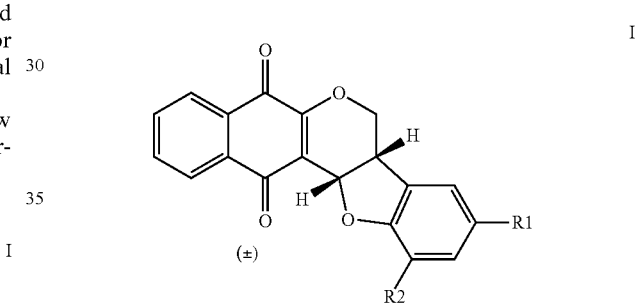

I (±)

and/or its salts, solvates and racemates in the manufacture of a drug aimed at treating diseases and/or systemic dysfunctions related to phenomenon of undesired cell proliferation such as neoplasm and parasitic infections in human and non-human mammals.

The sixth object of this invention is the use of new compounds of formula (I):

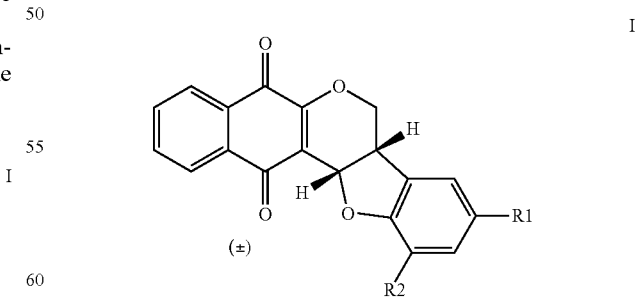

I (±)

and/or its salts, solvates and racemates, pharmaceutically acceptable, alone or a combination thereof for the manufacture of a drug aimed at treating diseases and dysfunctions related to increased levels of TNF-α in human or nonhuman mammals.

It is also an object of this invention, a drug containing a pharmaceutically acceptable amount of one or more of new compounds of pterocarpanquinone family with formula (I).

The eighth object of this invention relates to a method of treating diseases and dysfunctions related to the phenomenon of undesired cell proliferation such as neoplasm and parasitic infections in mammals.

The last object of this invention relates to a method of treating a disease or disorder relating to increased levels of TNF-α in mammals.

FIGURES

FIG. 1: Cytotoxic effects of the compound in an LBQ different neoplastic cell lines, K562 in A, B=in Lucena in B, Daudi in C and HL60 in D.

Figure 2:
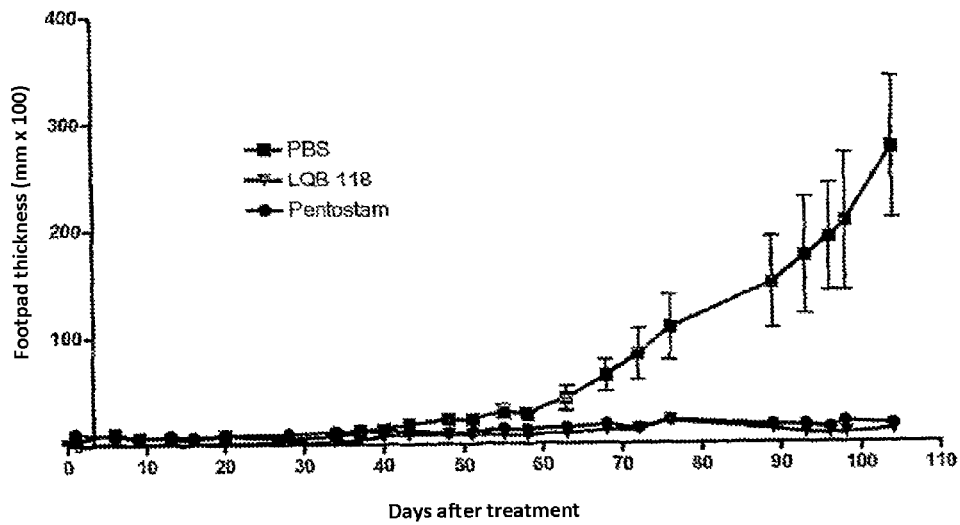

FIG. 2: Verification in vivo of LQB1 pterocarpanquinone efficacy in leishmaniasis cells.

Figure 3:
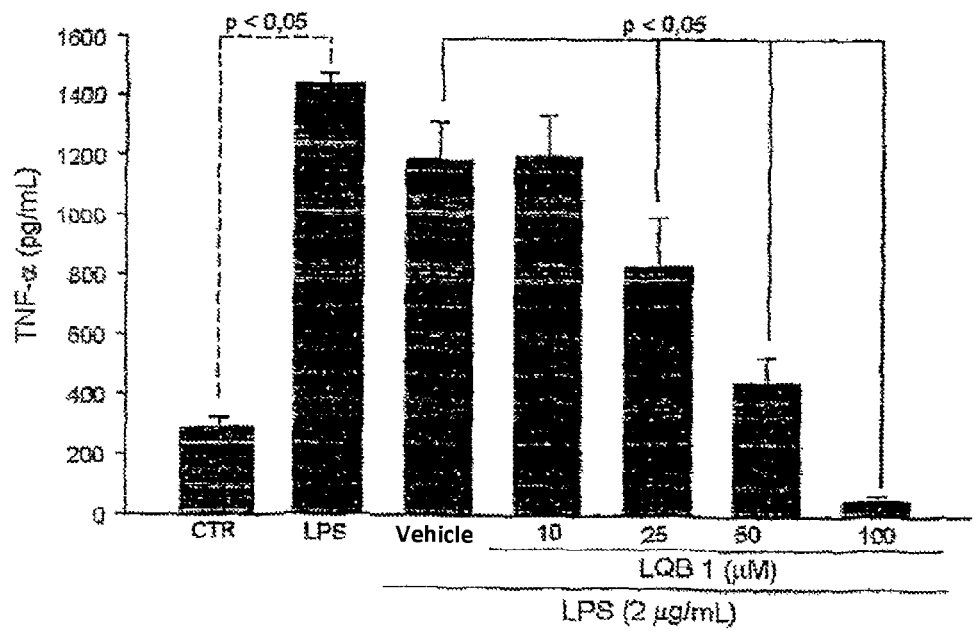

FIG. 3: In vitro effect of a LQB in inhibiting release of TNF-α by PBMC. The results are expressed as mean±standard error. (# In the control group; § in the groups incubated with LQS 1, $p<0.05$).

Figure 4:
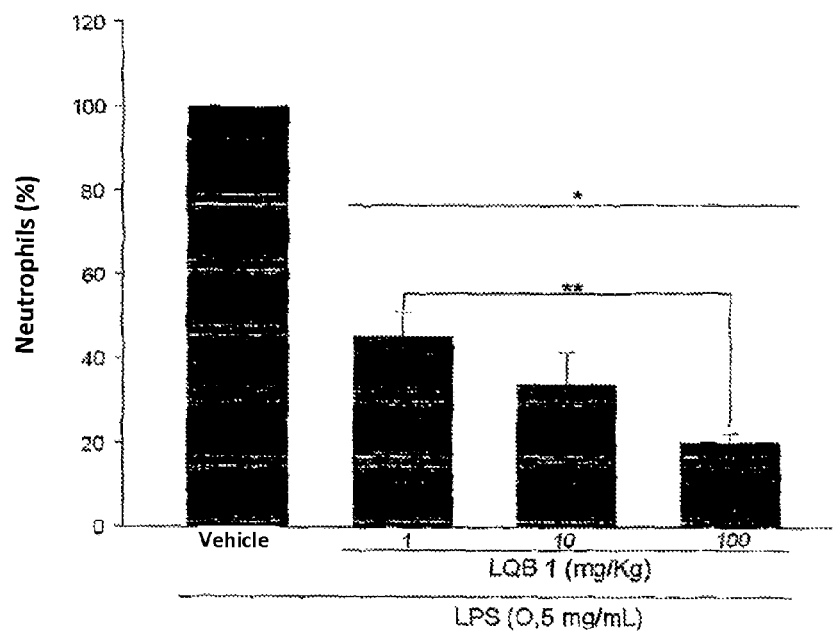

FIG. 4: in vivo effect of LQS 1 in inhibiting the release of neutrophils in LBA. The results are expressed as mean±standard error. (* compared to vehicle group, ** compared to the group incubated with 1 mg/kg (LC50 dose), $p<0.05$).

DETAILED DESCRIPTION OF THE INVENTION

The present invention aims to describe new compounds of pterocarpanquinone family with general formula (I):

I where:

R1 can be H; hydroxyl, C1 to C8 alkyl cyclic or aliphatic; C3 to C8 aryl cyclic or aliphatic; C3 to C8 alkenyl cyclic or aliphatic; C3 to C8 alkenyllil cyclic or aliphatic; an ether group C2 to C8; formyl; alkali metal; alkaline earth metal; halogen; nitro; amino; amine; C02R3; an alcohol group C1 to C8;

R2 can be H; hydroxyl, C1 to C8 alkyl cyclic or aliphatic; C3 to C8 aryl cyclic or aliphatic; C3 to C8 alkenyl cyclic or aliphatic; C3 to C8 alkenylil cyclic or aliphatic; an ether group C2 to C8; formyl; alkali metal; alkaline earth metal; halogen; nitro; amino; amine; an alcohol group C1 to C8; and R3 can be H; C1 to C8 alkyl cyclic or aliphatic, C3 to C8 aryl cyclic or aliphatic; C3 to C8 alkenyl cyclic or aliphatic; C3 to C8alkenyllil cyclic or aliphatic; alkali metal; alkaline earth metal and halogen.

Where the new compound of pterocarpanquinone family with general formula (I):

I can be presented in their salts, solvates and racemates form.

Preferably R1 can be H; hydroxyl, C1 to C6 alkyl cyclic or aliphatic; an ether group C2 to C6; formyl; alkali metal; halogen; nitro; amino; amine; C02R3; an alcohol group C1 to C6;

R2 can be H; hydroxyl, C1 to C6 alkyl cyclic or aliphatic; an ether group C2 to C6; formyl; and, R3 can be H; OH, C1 to C3 alkyl cyclic or aliphatic; alkali metal and halogen.

More preferably R1 can be H; hydroxyl, C1 to C6 alkyl cyclic or aliphatic; an ether group C2 to C6; formyl; alkali metal; halogen; nitro; amino; amine; C02R3; an alcohol group C1 to C6;

R2 can be H; hydroxyl, an ether group C2 to C6; formyl; and,

R3 can be H; C1 to C3 alkyl cyclic or aliphatic; Na; K and halogen.

The referred compounds of pterocarpanquinone family with general formula (I):

I which are objects of this invention capable to be activated by reduction, generating alkylating species intracellularly, which is directly related to damage both the structure of the DNA molecule as in the enzymatic machinery responsible for DNA replication. Thus, these compounds of pterocarpanquinone family with formula (I), object of this invention, promote cell cycle arrest, stopping the proliferation of cells from human and/or nonhuman mammals to divide continuously, that means, cells with undesirable proliferation.

New compounds of pterocarpanquinone family with general formula (I):

I are able to present selective cytotoxic effect, capable of stopping the cell cycle in continuously dividing cells, such as tumor cells and cells of parasites in general. However, do not exhibit toxicity to lymphocytes activated by PHA of human and/or non-human mammals, also found in quick proliferation.

It was also demonstrated in tests that the effect of new compound of pterocarpanquinone family with general formula (I):

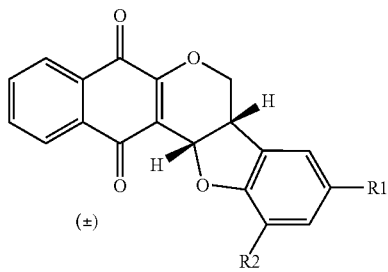

object of this invention have lead to reduced levels of alpha tumor necrosis factor (TNF-α) in vivo in humans and/or nonhumans mammals.

Therefore, the new compounds of pterocarpanquinone family described herein can be employed to treat diseases and/or dysfunctions related to the phenomenon of undesired cell proliferation such as tumors and parasites. They can be used to treat diseases and/or dysfunctions related to high levels of TNF-α, for example: diseases and inflammatory dysfunctions in general, preferably, in diseases and/or dysfunctions caused by reactive inflammatory infestation of parasites in body of a human and/or nonhuman mammals.

Only for the purposes of this invention, parasitic are those diseases or dysfunctions caused by unicellular organisms belonging to bacteria and protista kingdoms in mammals, human or nonhuman.

Preferably new compounds of formula (I):

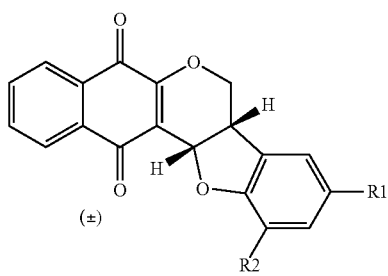

can be used in treating tumors resistant to multiple drugs (MOR) such as, leukemia, solid tumors in organs such as lung, breast, liver, among others. Still preferably, this invention are parasitic diseases or dysfunctions within the group of diseases or dysfunctions that include leishmaniasis, malaria, Chagas disease, toxoplasmosis, leprosy, tuberculosis, brucellosis, among others.

This invention also provides a production process of new compounds of pterocarpanquinone family with general formula (I):

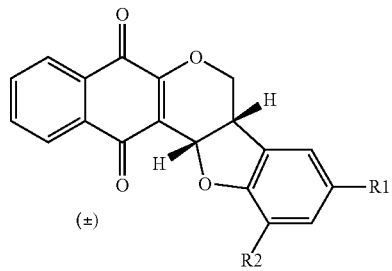

and/or its salts, solvates and racemates using synthetic procedure environmentally friendly and economically appropriate because the use of catalysts based on palladium in catalytic amounts and the lack of reagents containing mercury.

Production process of new compounds of pterocarpanquinone family with general formula (I):

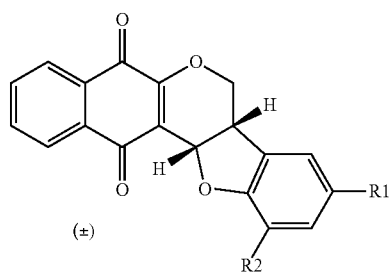

as well as its salts, solvates and racemates, object of this invention, presents the steps of:
 a) Synthesis of intermediate 1;
 b) Purification of intermediate 1;
 c) Synthesis of compounds of formula (I);
 d) Purification of compounds of formula (I).

The step a) occurs from the reaction between acrolein and lawsone in the presence of a solvent and an acidic solution to reflux for a period of time between 2 to 12 hours.

The solvents that can be employed in this stage of the process of obtaining new pterocarpanquinone of formula (I) of this invention are organic solvents such as benzene, acetone, toluene, methanol, ethanol and others. Preferably the organic solvent used is toluene. The acid solution used in this step may contain organic acids such as acetic acid, formic acid, fumaric acid, phenyl boronic acid, valeric acid, acrylic acid, propionic acid, benzoic acid, oxalic acid, succinic acid, "terephthalic" acid, fumaric acid, trichloroacetic acid, tartaric acid, among others. Preferably, the acidic solution used in this step is a solution containing at least acetic acid and phenyl boronic acid and the reaction period is less than 6 hours.

In step b) the product obtained in a) is concentrated and purified with the aid of organic phase extractor agents. The concentration can be obtained by means of man art known, for example, by using rotary evaporators.

The extractor agents can be used in purification, for example, ethers, esters and alcohols, preferably employing ethyl acetate as extracting agent. Next phase is washed successively with one or more organic salts and/or inorganic salts, preferably to employ sodium bicarbonate and sodium chloride. Drying agents that can be employed are those known by man's art, for example, magnesium sulfate, copper sulfate, calcium chloride and silica. Is employed in this invention preferably sodium sulfate.

The intermediate 1, produced according to steps a) and b), is the "chromenoquinone" to serve as a substrate for the start of step c) reaction.

The step c) occurs by the reaction of oxa-Heck catalytic, involving "chromenoquinone" with a phenol ortho-substituted by halogen, in the presence of an organic solvent, a metal salt and phosphine in the presence of stoichiometric amounts of a catalyst on a period between 1 to 24 hours under reflux in a modified atmosphere.

The phenol ortho-substituted by halogen preferably employed in this invention is ortho phenol-iodine. It can be substituted or not substituted on carbons 3 and 5 of the aromatic ring. The organic solvent used in this step can be selected from the group containing benzene, acetone, toluene, methanol, ethanol, among others. Preferably acetone is used as a solvent.

For purposes of this invention, substoichiometric amount of catalyst means the lower molar proportion of catalyst required for the reaction to occur with maximum possible yield.

The catalyst employed in this invention is a catalyst containing palladium, may be palladium chloride or palladium acetate. Palladium acetate is preferably used as catalyst in this invention.

The metal salt employed in step c) is a noble metal salt. Preferably, silver carbonate is employed under reflux for a period from 80 to 20 hours in a nitrogen atmosphere.

A second period of reflux can be performed under the same conditions as the first reflow from step c) with the addition of an excess amount of phenol ortho-substituted by halogen to the reaction field for the maximum utilization of "chromenoquinone".

The step d) occurs in a manner analogous to step b) obtaining new compounds of pterocarpanquinone family of formula (I), object of this invention.

An alternative procedure for synthesis of new compounds of formula (I):

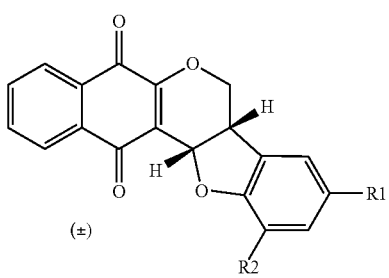

this invention, occurs by the use of "chromenodimetoxi" in step c), who happens to be methylated and reduced form of "chromenoquinone", as a starting point. The catalytic conditions employed for the use of "chromenodimetoxi" are identical to conditions used by "chromenoquinone".

A pharmaceutical composition containing the new compounds of formula (I):

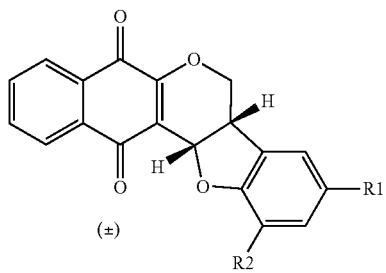

and/or its salts, solvates and racemates, pharmaceutically acceptable, alone or a combination thereof in an amount pharmaceutically acceptable and non-active compounds, pharmaceutically acceptable, aimed to treat diseases or dysfunctions related to the phenomenon of undesired cellular proliferation in human and/or nonhuman mammals, is an object of this invention.

A pharmaceutical composition containing the new compounds of formula (I):

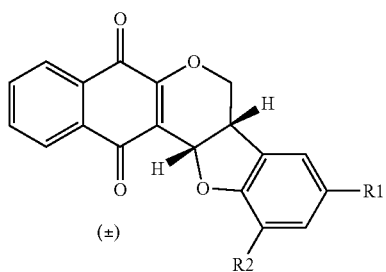

and/or its salts, solvates and racemates, pharmaceutically acceptable, alone or a combination thereof in a pharmaceutically acceptable amount. In addition to pharmaceutically acceptable non-active compounds targeted to treat diseases or dysfunctions related to increased levels of TNF-α in human or nonhuman mammal is another object of this invention.

For this invention, we have a pharmaceutically acceptable amount of new compounds of formula (I). Is between 0.05 µM to 1M in one of the new compounds of formula (I) or a combination of different new compounds of pterocarpaquinonas family of formula (I) of this invention.

Preferably, it is understood by pharmaceutically acceptable amount, the concentration between 0.5 to 750 µM of compounds of formula (I), more preferably still, the pharmaceutical composition containing between 1 to 450 µM of one of the new compounds of formula (I); or a combination of different new compounds of pterocarpaquinonas family of formula (I) of this invention.

Also for purposes of this invention, pharmaceutically acceptable non-active compounds may be those compounds known to man of art, which are usually employed in the pharmaceutical industry, such as adjuvants, diluents, preservatives, antioxidants, antimicrobial agents, sweeteners, flavorings, dispersing among others.

Use of new compounds of formula (I):

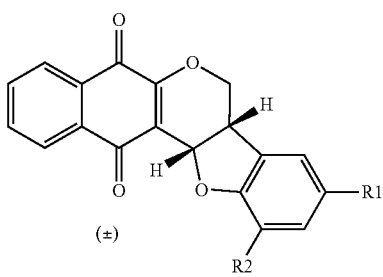

and/or its salts, solvates and racemates, pharmaceutically acceptable, alone or a combination thereof for the manufacture of a drug aimed at treating diseases and dysfunctions related to the phenomenon of undesired cell proliferation such as neoplasm and parasitic infections in mammals, human or not humans, is also an object of this invention.

It is also an object of this invention the use of new compounds of formula (I) and/or its salts, solvates and racemates, pharmaceutically acceptable, alone or a combination thereof for the manufacture of a drug aimed at treating diseases and dysfunctions related to increased levels of TNF-α in human and nonhuman mammals.

For this invention, the product must contain a pharmaceutically acceptable amount of one or more of new compounds of pterocarpanquinone family with general formula (I):

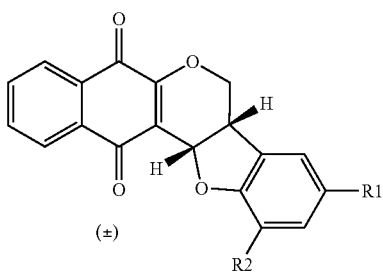

can be found in all dosage forms of art known to man. They could be used as a liquid, semisolid or solid. For example: in the form of solutions, injectable solutions, potions, resulting suspension, emulsions, tinctures, elixirs, syrups, tablets, pills, tablets, wafers, pills, beads, pills, capsules, powders, eggs, cream, poultice, ointment, cerate, liniments, pastes, lotions, ointments, gels, sprays, patches (nicotine) patches, ampoules, sprays, and others.

A method of treating a disease or disorder related to the phenomenon of undesired cellular proliferation, comprising administering a therapeutically acceptable amount of new compounds of formula (I):

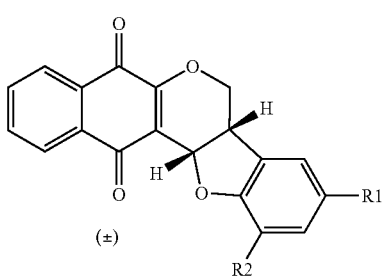

and/or its salts, solvates and racemates, pharmaceutically acceptable, alone or a combination thereof, to a human or nonhuman mammal carrying a disease or disorder related to the phenomenon of undesired cellular proliferation.

A method of treating a disease or systemic disorder relating to increased levels of TNF-α comprising administering a therapeutically acceptable amount of new compounds of formula (I):

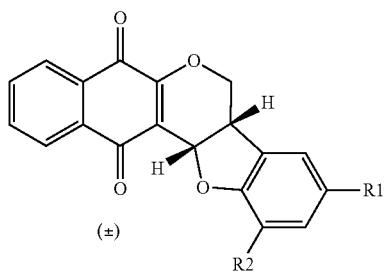

and/or its salts, solvates and racemates, pharmaceutically acceptable, alone or a combination of them, to human or nonhuman mammal patients with diseases or systemic dysfunctions related to increased levels of TNF-α.

The diseases or dysfunctions related to both the phenomenon of undesired cellular proliferation as increased levels of TNF-α to which this invention relates are neoplasms and parasitic diseases. Preferably this invention neoplasms are tumors resistant to multiple drugs (MOR), such as leukemia and solid tumors in organs such as lung, breast, liver and other organs and tissues, and parasites are understood group of diseases or dysfunctions such as leishmaniasis, malaria, Chagas disease, toxoplasmosis, leprosy, tuberculosis, brucellosis and other diseases and/or dysfunctions caused by infestation with parasites in the body of a host animal, like a human or nonhuman mammal.

The following examples are merely illustrative embodiments of this invention and should not be used in limiting the rights of inventors.

Example 1

New Pterocarpanquinone Produced by Formula (I)

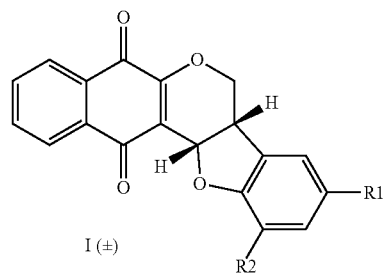

| Compound | R1 | R2 | R3 |
|---|---|---|---|
| LQB1 | H | H | — |
| LQB2 | $NO_2$ | H | — |
| LQB3 | $NH_2$ | H | — |
| LQB4 | $CO_2R_3$ | H | $CH_3$ |
| LQB5 | $CO_2R_3$ | H | H |
| LQB6 | $CO_2R_3$ | H | Na |
| LQB7 | $CH_2OH$ | H | — |
| LQB8 | CHO | $H_3CO$ | — |
| LQB9 | $CO_2R_3$ | $H_3CO$ | Na |

Formula (I)

[Structure of Formula (I) with R1, R2 substituents]

I (±)

| Compound | R1 | R2 | R3 |
|---|---|---|---|
| LQB10 | Cl | H | — |
| LQB11 | Br | H | — |

Example 2

Synthesis of Compounds of Formula (I)

2.1—Synthesis of Intermediate 1
(a-dehydro-desmethyl-lapachone)

Lawsone solution (1.0 g, 5.74 mmol), acrolein (13.2 mL), phenyl boronic acid (0.7 g, 5.74 mmol) and glacial acetic acid (26.4 mL) in toluene (210.0 mL) was refluxed for 6 hours. The product formation was monitored by TLC. The reaction mixture was cooled, concentrated in a rotary evaporator and extracted with ethyl acetate. The organic extract was washed successively with $NaHCO_3$ and saturated NaCl solution, dried on $Na_2SO_4$ and the solvent evaporated. The crude material was purified by column chromatography giving a red solid (0.6 g, 50% yield), fp=215-217° C.

2.1—Synthesis of LQBs

Synthesis of LQB1 by a solution of chromenequinone (106 mg, 0.5 mmol) in acetone (50 mL) under stirring. Were added 83 mg of o-iodophenol (0.75 mmol), 413 mg $Ag_2CO_3$ (1.5 mmol), 26.2 mg of $PPh_3$ (0.1 mmol, 20 mol %) and 11.2 mg of $(AcO)_2Pd$ (0.05 mmol, 10 mol %). The reaction mixture was refluxed for 16 hours under $N_2$ atmosphere. After this time, analysis by TLC indicated the formation of a product slightly less polar than the chromenequinone, however there was still a significant amount of the chromenequinone. Over 83 mg (0.75 mmol) of o-iodophenol were added to the reaction. This new mixture was refluxed for another 16 hours, whereupon TLC analysis indicated the total consumption of cromenoquinona. The solvent was evaporated in a rotary evaporator, the product extracted with ethyl acetate, the organic phase washed with saturated NaCl and dried on $Na_2SO_4$. After purification by column chromatography were obtained 62.3 mg (0.21 mmol) of LQB 1 in 41% yield. fp: 145° C., m/z 304.

For other LQBs synthesis the process employed is the same. The only modification is the ortho-iodine phenol employed. As described for the synthesis of other employees are LQBs The iodine-substituted phenols or substituted on carbons 3 and 5 of the aromatic ring. The table below shows some of LQBs obtained, and the iodine-phenol used in its synthesis.

| LBQ s Production | |
|---|---|
| Obtained Compound | Ortho-iodine phenol employed |
| LBQ 2 | [4-nitro-2-iodophenol structure] |
| LBQ 4 | [methyl 4-hydroxy-3-iodobenzoate structure] |
| LBQ 8 | [2-methoxy-4-formyl-6-iodophenol structure] |
| LBQ10 | [4-chloro-2-iodophenol structure] |

2.3—Alternative Process Synthesis

The agitation in a solution of cromenodimetoxi (0.5 mmol) in acetone (50 mL) under stirring were added 83 mg of o-iodophenol (0.75 mmol), 413 mg $Ag_2CO_3$ (1.5 mmol), 26.2 mg of $PPh_3$ (0.1 mmol, 20 mol %), and 11.2 mg of $(AcO)_2Pd$ (0.05 mmol, 10 mol %). The reaction mixture was refluxed for 16 hours under $N_2$ atmosphere. After this 16 hours the solvent was evaporated in a rotary evaporator, the product extracted with ethyl acetate, the organic phase washed with saturated NaCl solution and dried under $Na_2SO_4$. The crude product was treated with CAN (1.0 mmol) in dichloromethane (10 mL) as solvent at ambient temperature for a period of 12 hours. After this time the product was obtained under the conditions described above. After purification by column chromatography were obtained (0.29 mmol) of LBQ1 in 49% yield. fp: 145° C.

Example 3

Clinical Trials 3.1—Cancer 3.1.1—Cell Lines and Cell Culture

It was used the established cell lines K562, Lucena-1, Daudi, Raji, Jurkat and HL-60. The cells are grown in bottles of 25 $cm^3$, 5 mL of RPMI medium supplemented with 10% fetal calf serum (FCS). The number of cells was counted by light microscopy in a Neubauer chamber and adjusted to a concentration of 2×104 cells/mL before the bells. (held twice a week) For the Jurkat line, the amount of cells was adjusted to 2×105 cells/mL. The strain named Lucena-1 was selected from a sample of K562, which was exposed to increasing concentrations of VCR, starting by 3 nM up to 60 nM, from which the surviving cells were maintained. In addition to the culture field and FBS, for Lucena-1 cultures, 60 nM of VCR were added. The cultures are incubated in 5% $CO_2$ at 37° C.

3.1.2—Measurement of Cell Viability

In order to measure cell viability after incubation with synthetic pterocarpanes, leukemic cells were tested using the MTT colorimetric assay (3,4,5-bromide dimetiazol-2-yl-2,5-"diphenyltetrazol") (Mosmann, 1983; Denizot, 1986; Barile, 1994). The plates containing cells, also at a concentration of $2 \times 10^4$ cells/mL were incubated in the oven for 72 hours in the presence of substances. The line Jurkat was incubated at a concentration of $2 \times 10^5$ cells/mL, and peripheral blood lymphocytes $10^6$ cells/mL solution of MTT was prepared at a concentration of 5 mg/mL diluted in saline solution, and subsequently added to the cells in the amount 20 mL per well of ELISA plate. We anticipated three hours after this incubation and the plates were then centrifuged at 1500 rpm for 7 minutes. The supernatant was discarded after centrifugation. The MTT mitochondrial dehydrogenase reacts with reducing tetrazolium salts, generating as a result of crystal blue-purple "formazan" were then dissolved in 200 mL of DMSO.

After this procedure the intensity of color formed could be measured in ELISA reader at a wavelength of 490 nm. As white, discounted values obtained was used only half and 10% FCS, and as controls, only cells in the absence of compounds. The readings were done in triplicate.

3.1.3—Collection of Peripheral Blood Lymphocytes Activated

Peripheral blood was obtained from healthy donors using heparinized syringe, in order to prevent coagulation, and stored in tubes of 15 mL. To these tubes was added histopaque, a substance capable of forming a density gradient that allows the separation of different cell types of the blood. The blood was centrifuged with histopaque for 30 minutes at 1500 rpm. Precipitate is found in red cells and polymorphonuclear cells in the majority, while the supernatant is basically composed by the plasma and a histopaque. Between these two layers is formed an interface which can be extracted from mononuclear cells. These were washed in PBS and then re-suspended in RPMI field with 10% fetal calf serum. Mononuclear cells (lymphocytes 80%) were then adjusted to a concentration of $1 \times 10^6$/mL, a concentration of these cells circulating in the blood. Incubation with the compounds occurred in the presence of 5 mg/mL of phytohemagglutinin (PHA), a known agent "mitogen", since dividing cells are usually more sensitive to chemotherapy in general.

3.2—*Leishimania*

3.2.1—Maintenance of Parasites

The causative agent was cultured in vitro according to the technique described by Trager & Jensen (1976) which consists in maintaining the parasite in a suspension of RBCs to 370° C., under sterile conditions in an atmosphere of 5 to 10% $CO_2$ and approximately 5% $O_2$.

Solutions with different concentrations (0.1-1000 μg-mL) of each sample to be tested were sterilized by gamma irradiation. It was added 100 mL of a suspension of 2% 0+ erythrocytes and 0.2% of parasitemia to the wells of culture plates. Thenwere added 10 mL of solutions containing the samples under test or reference drug. (Artesunate, mefloquine or chloroquine—50 nM) according (Desjardins, 1979) and (Chulay, 1982). After 72 hours incubation at 370° C. in an atmosphere of 10% of CO2 and approximately 5% of O2, a small aliquot of the suspension will be collected with the aid of Pasteur pipette and placed on slides to perform smear to be stained by May-GrunwaldGiemsa. Parasitemia is determined by the following equation:

$$\% PA = \frac{HA \times 100}{HC}$$

PA: Parasitemia
HA: Number of samples of parasitized red blood cells treated.
HC: Number of parasitized red blood cells without treatment

3.2.2—Production of Nitric Oxide

The nitric oxide production was estimated indirectly by measuring the concentration of nitrite in culture supernatants of macrophages. The murine peritoneal macrophages are obtained and plated in 96-well plates. After removal of non-adherent cells, macrophages are infected or not and the selected molecules are added at various concentrations (1-100 μM). After 72 h, the plates are centrifuged and the supernatant is evaluated colorimetrically as nitrite concentration by adding Griess reagent. The absorbance is measured at a wavelength of 570 nm. The production of nitric oxide is an important mechanism of macrophage leishmanicidal and serves as a parameter for evaluating the state of activation.

3.2.3—In Vitro Test

Total lymph node cells (mainly lymphocytes) from mice were plated in 96-well plates at 37° C., with these molecules in various concentrations (1-100 μM), with the stimulus or not of concanavalin A. After 72 h, cell viability is estimated colorimetrically by the amount of lactate dehydrogenase (LDH) released in culture supernatants.

3.2.4—In Vivo Test

The selected molecules were tested in an experimental model of murine cutaneous leishmaniasis. BALB/c mice are infected with *L amazonensis* in the ear-GFP and treated by intralesional injections with the molecules adopted in the previous steps. Treatment efficacy was monitored by two parameters: a) growth of the lesion measured with a caliper, and b) parasite load measured by fluorimetry, as previously established methodology (Boek, 2006).

3.3—Toxoplasmosis

3.3.1—Collection of Tachyzoites of *Toxoplasma Gondij*

Tachyzoites of *T. gondii* (RH strain) will be maintained by passages in the peritoneal cavity of mice every 2 or 3 days. After this period, will be done by injecting peritoneal lavage 3 mL of Hank. The wash is centrifuged at 100 g for 5 min, the supernatant collected and centrifuged at 1000 g for 10 minutes. The parasites will be re-suspended in DMEM and counted.

3.3.2—Peritoneal Macrophages

Peritoneal macrophages are obtained by peritoneal lavage of Swiss mice (CF1) with 5 mL of Hank. The macrophages are plated on glass coverslips in 24-well plates. After 1 hour of adherence at 37° C., cells are washed with Hank at 37° C. and grown to Dulbecco's Modified Eagle's Medium (DMEM) containing 5% fetal calf serum (FCS) at 37° C. in an atmosphere of 5% $CO_2$.

3.3.3—Activation of Peritoneal Macrophages and Interaction with Parasites

Interactions will be made with resident macrophages or activated with 50 U/mL of recombinant interferon-γ mice (IFN-γ; Sigma) and 100 ng/mL of bacterial lipopolysaccharide (LPS, Sigma). To prove the involvement of nitric oxide (NO) in the destruction of the protozoa utilize$^{NG}$monomethyl L-arginine (LNMA-SIGMA) that blocks the production of NO. After activation of macrophages, 1 mg/mL LNMA will be added to the culture medium.

3.3.4—Preparation for Observation of Interactions in Optical Microscopy

After the different interaction points, the cells are fixed in Bouin's solution (70% saturated solution of picric acid, 23% formalin and 7% acetic acid), washed, stained with Giemsa solution (diluted in distilled water at 1:10), dehydrated in a series of acetone-xylene solution, mounted on Entellan and observed under an optical microscope. The stained cells will be quantified as follows: a) % of macrophages with parasites, b) % of macrophages without parasites and c) number of parasites per macrophage. These results of quantification are used to analyze the development of infection and survival of the parasites.

3.3.5—Preparation for Observation of Interactions in Electronic Microscopy

After different points of interactions with different treatments, the cells are affixed to the method karnowski (2.5% glutaraldehyde, 4% paraformaldehyde in sodium cacodylate buffer 0.1 M). After fixation, the cells are washed in sodium cacodylate buffer and then post-fixed in osmium tetroxide 1%. After the fixation process, cells will be dehydrated in a series of concentrations of acetone and then embedded in epoxy resin. After ultramicrotomy, the cuts will be contrasted in uranyl acetate and lead citrate and then observed in transmission electronic microscopy.

3.3.6—Growing LLCMK2

Cultivation of fibroblast cells in vitro LLCMK2 was made with DMEM supplemented with 5% Fetal Bovine Serum. The cells were grown in 5% CO2 atmosphere.

3.3.7—Interaction Parasito-Cell

The interactions of macrophages with *Toxoplasma gondii* or LICMK2 fibroblast cells were performed on 1, 24 and 48 hours of interaction. All interactions were performed in the presence or absence of drug LQB-118 according to the results presented.

3.4—Action of New Pterocarpanquinone from Formula (I) on TNF

3.4.1—Inhalation of LPS

For inhalation of LPS, we used a glass inhalation chamber with a volume of 1 liter, with a capacity of 8 mice. The mice were placed in this chamber for five minutes and inhaled aerosols produced by positive pressure of 2 mL of a suspension of LPS containing 0.5 mg/mL, prepared in physiological saline (NaCl 0.9%). The control group inhaled saline only.

3.4.2—Treatment with LQB

Groups of animals were treated with LQB dissolved in physiological saline with 10% ethanol (vehicle) at doses of 1, 10 and 100 mg/kg. The substances were administered in a volume of 200 μL intraperitoneal (ip) 1 hour before LPS inhalation. In parallel, groups of animals were treated with 200 μL of the vehicle.

3.4.3—Bronchoalveolar Lavage (BAL)

Three hours after inhalation of LPS, animals were sacrificed by cervical dislocation, their tracheas were exposed, cannulated and lungs were washed with saline to a final volume of 1.5 mL in tubes kept at 4° C. (FIG. 10). An aliquot of 300 μL of lavage was used to count and identify the cells and the remainder was centrifuged at 1,500×g for 10 minutes (Sorvall, USA). The supernatant was stored at −20° C. for subsequent cytokine.

3.4.4—Cells Count

The total number of cells was determined in a cell counter type Coulter Counter (Coulter Electronics Inc.—USA). The identification of different cell types present in BAL cytospin was made after 200 μl of LBA at 80×g for 1 minute (Shandon—USA). The slides prepared from cytospin stained with Diff-Quick kit (Shandon, USA).

We counted approximately 200 cells on each slide. The identification of cell type was based on the morphological descriptions as described by Stevens and Lowe (1995).

3.4.5—Collection of Mononuclear Cells from Human Peripheral Blood (PBMC)

Mononuclear cells were obtained from peripheral blood of healthy donors by gradient centrifugation in Ficoll. 20 ml peripheral blood were carefully added to 16 mL of Ficoll followed by centrifugation at 1500×g for 30 minutes. Once collected, the PBMC were washed twice with saline and resuspended in culture field RPMI 1640 containing 0.1 mg streptomycin/mL, penicillin 100 U/mL and supplemented with 10% of FCS.

3.4.6—LPS Incubation in Vitro

The PBMC resuspended in RPMI were seeded in 24-well plate ($8\times10^5$ cells/well). The cells were incubated with LPS at a concentration of 2 μg/mL at 37° C. in 4% $CO_2$ for 2 hours. After incubation with LPS, the supernatant was collected and centrifuged at 14,000×g for 1 minute to rule out any possible cell. The supernatant was stored at −20° C. for subsequent cytokine.

3.4.7—In Vitro Incubation with LQB

The groups received cells treated concomitantly with stimulation of LPS, LQB diluted in 0.5% DMSO (vehicle) at concentrations of 10, 25, 50 and 100 μM. A group of cells received only the vehicle.

The invention claimed is:

1. A pterocarpanquinone compound of formula (I):

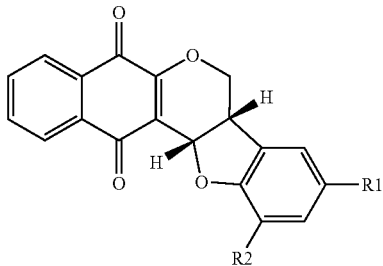

where:
- R1 can be H; hydroxyl, C1 to C8 alkyl cyclic or aliphatic; C3 to C8 aryl cyclic or aliphatic; C3 to C8 alkenyl cyclic or aliphatic; C3 to C8 alkynyl cyclic or aliphatic; an ether group C2 to C8; formyl; alkali metal; alkaline earth metal; halogen; nitro; amino; amine; $CO_2R3$, or an alcohol group C1 to C8;
- R2 can be H; hydroxyl, C1 to C8 alkyl cyclic or aliphatic; C3 to C8 aryl cyclic or aliphatic; C3 to C8 alkenyl cyclic or aliphatic; C3 to C8 alkynyl cyclic or aliphatic; an ether group C2 to C8; formyl; alkali metal; alkaline earth metal; halogen; nitro; amino; amine; or an alcohol group C1 to C8; and
- R3 can be H; C1 to C8 alkyl cyclic or aliphatic, C3 to C8 aryl cyclic or aliphatic, C3 to C8 alkenyl cyclic or aliphatic; C3 to C8 alkynyl cyclic or aliphatic; alkali metal; alkaline earth metal; or halogen;

including a salt, solvate or racemate of formula (I).

2. The compound of claim 1, wherein:
- R1 is H; hydroxyl, C1 to C6 alkyl cyclic or aliphatic; alkali metal; halogen; nitro; amino; amine; $CO_2R3$, or an alcohol group C1 to C6; and,
- R2 is H; hydroxyl, C1 to C6 alkyl cyclic or aliphatic; an ether group C2 to C6; or formyl; and
- R3 is H; C1 to C3 alkyl cyclic or aliphatic, alkali metal or halogen.

3. The compound of claim 1, wherein:
- R1 is H; hydroxyl, C1 to C6 alkyl cyclic or aliphatic; nitro; amino; amine; $CO_2R3$, an ether group C2 to C6; an alcohol group C1 to C6; or formyl, and,
- R2 is H; hydroxyl, formyl; or an ether group C2 to C6; and
- R3 is H; C1 to C3 alkyl cyclic or aliphatic, Na; K; or halogen.

4. The compound of claim 1, wherein the compound has a cytotoxic effect in human or non-human mammals.

5. The compound of claim 4, wherein the compound is antiproliferative.

6. The compound of claim 1, wherein the compound reduces levels of alpha tumor necrosis factor (TNF-α) in vivo in humans and nonhumans mammals.

7. The compound of claim 1, comprising the ability to be employed to treat diseases and/or dysfunctions related to undesired cell proliferation, and the ability to be used to treat diseases and/or dysfunctions related to high levels TNF-α in host humans and/or nonhumans mammals.

8. The compound of claim 7, wherein the diseases and/or dysfunctions related to undesired cell proliferation are neoplasm and parasitoses.

9. The compound of claim 8, wherein the parasitoses are diseases or dysfunctions within the group of diseases or dysfunctions that include leishmaniasis, Chagas disease, and toxoplasmosis.

10. The compound of claim 8, wherein the neoplasms are tumors resistant to multiple drugs (MDR) including leukemia and solid tumors in organs including the lung, breast, and liver.

11. Process for production of a pterocarpanquinone compound of general formula (I),

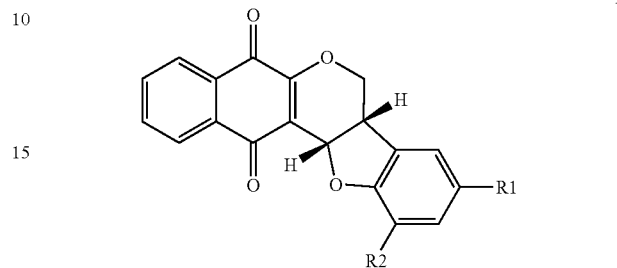

comprising the steps of:
a) reacting acrolein and lawsone in the presence of a solvent and an acidic solution to reflux for a period of time between 2 to 12 hours to produce a chromenoquinone;
b) purifying the chromenoquinone;
c) synthesizing a compound of the formula (I) from the chromenoquinone; and
d) purifying the compound of the formula (I);

wherein:
- R1 can be H; hydroxyl, C1 to C8 alkyl cyclic or aliphatic; C3 to C8 aryl cyclic or aliphatic; C3 to C8 alkenyl cyclic or aliphatic; C3 to C8 alkynyl cyclic or aliphatic; an ether group C2 to C8; formyl; alkali metal; alkaline earth metal; halogen; nitro; amino; amine; $CO_2R3$; or an alcohol group C1 to C8;
- R2 can be H; hydroxyl, C1 to C8 alkyl cyclic or aliphatic; C3 to C8 aryl cyclic or aliphatic; C3 to C8 alkenyl cyclic or aliphatic; C3 to C8 alkynyl cyclic or aliphatic; an ether group C2 to C8; formyl; alkali metal; alkaline earth metal; halogen; nitro; amino; amine; or an alcohol group C1 to C8; and
- R3 can be H; C1 to C8 alkyl cyclic or aliphatic, C3 to C8 aryl cyclic or aliphatic, C3 to C8 alkenyl cyclic or aliphatic; C3 to C8 alkynyl cyclic or aliphatic; alkali metal; alkaline earth metal; or halogen;

including a salt, solvate or racemate of formula (I).

12. The process according to claim 11, wherein the solvent of step (a) is an organic solvent.

13. The process according to claim 12, wherein the organic solvent is toluene.

14. The process according to claim 12, wherein the acidic solution comprises one or more organic acids selected from the group consisting of acetic acid, formic acid, fumaric acid, phenyl boronic acid, valeric acid, acrylic acid, propionic acid, benzoic acid, oxalic acid, succinic acid, terephthalic acid, fumaric acid, trichloroacetic acid, and tartaric acid.

15. The process according to claim 14, wherein the acidic solution comprises at least acetic acid and phenyl boronic acid.

16. The process according to claim 11, wherein the reflux period is less than 6 hours.

17. The process according to claim 11, comprising in the step (a) the concentration and purification of chromenoquinone.

18. The process according to claim 11, wherein the step (c) comprises reacting the chromenoquinone with a phenol ortho-substituted by halogen, in a second organic solvent, a metal salt and phosphine and in the presence of a stoichiometric amount of a catalyst for a period of time between 1 to 24 hours under reflux in a modified atmosphere.

19. The process according to claim 18, wherein the phenol ortho-substituted by halogen is an optionally substituted ortho phenol-iodo compound wherein the substituents are on carbons 3 and 5 of the aromatic ring.

20. The process according to claim 18, wherein the second organic solvent is acetone.

21. The process according to claim 18, wherein the catalyst is palladium and is in less than a stoichiometric amount.

22. The process according to claim 18, wherein the metal salt is silver carbonate.

23. The process according to claim 18, wherein the reaction is between 8 to 20 hours and the modified atmosphere is a nitrogen atmosphere.

24. The process according to claim 18, further comprising a second period of reflux, wherein an excess amount of phenol ortho-substituted by halogen is added.

25. The process according to claim 18, wherein the purification in step (b) and step (d) is performed using one or more organic phase extractor agents followed by successive washing with one or more organic or inorganic salts, and drying using a one or more drying agents.

26. A pharmaceutical composition comprising the compound of claim 1.

27. The pharmaceutical composition of claim 26, in the form of a solution, potion, suspension, emulsion, tincture, elixir, syrup, tablet, wafer, pill, bead, capsule, powder, cream, poultice, ointment, cerate, liniment, paste, lotion, ointment, gel, spray, or patch.

28. A method of treating cancers using the pharmaceutical composition of claim 26, wherein the cancers include leukemia and solid tumors in organs including the lung, breast, and liver.

29. A method of treating parasitic diseases using the pharmaceutical composition of claim 26, wherein the parasitic diseases include leishmaniasis, Chagas disease, and toxoplasmosis.

* * * * *